US010584360B2

(12) United States Patent
Medoff (10) Patent No.: US 10,584,360 B2
(45) Date of Patent: *Mar. 10, 2020

(54) COOLING AND PROCESSING MATERIALS

(71) Applicant: Xyleco, Inc., Wakefield, MA (US)

(72) Inventor: Marshall Medoff, Wakefield, MA (US)

(73) Assignee: Xyleco, Inc., Wakefield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/239,123

(22) Filed: Jan. 3, 2019

(65) Prior Publication Data

US 2019/0136268 A1 May 9, 2019

Related U.S. Application Data

(63) Continuation of application No. 15/586,159, filed on May 3, 2017, now abandoned, which is a continuation of application No. 13/532,976, filed on Jun. 26, 2012, now abandoned, which is a continuation of application No. PCT/US2011/020583, filed on Jan. 7, 2011.

(60) Provisional application No. 61/295,476, filed on Jan. 15, 2010.

(51) Int. Cl.
| | |
|---|---|
| *C12P 7/10* | (2006.01) |
| *C12P 7/16* | (2006.01) |
| *C12G 1/02* | (2006.01) |
| *C10G 1/00* | (2006.01) |
| *C10G 31/06* | (2006.01) |
| *C10G 32/04* | (2006.01) |
| *C12P 7/14* | (2006.01) |
| *C12P 19/02* | (2006.01) |
| *C12P 19/14* | (2006.01) |

(52) U.S. Cl.
CPC .............. *C12P 7/16* (2013.01); *C10G 1/002* (2013.01); *C10G 31/06* (2013.01); *C10G 32/04* (2013.01); *C12P 7/10* (2013.01); *C12P 7/14* (2013.01); *C12P 19/02* (2013.01); *C12P 19/14* (2013.01); *C10G 2300/1014* (2013.01); *C10G 2300/1025* (2013.01); *C10G 2300/308* (2013.01); *C10G 2300/4062* (2013.01); *C10G 2300/4068* (2013.01); *C12P 2201/00* (2013.01); *C12P 2203/00* (2013.01); *Y02E 50/10* (2013.01); *Y02E 50/16* (2013.01); *Y02E 50/17* (2013.01); *Y02P 30/20* (2015.11)

(58) Field of Classification Search
CPC ..... C12P 7/10; C12P 7/16; C12G 1/02; C12G 32/04; C12G 31/06
See application file for complete search history.

(56) References Cited

U.S. PATENT DOCUMENTS

| | | | |
|---|---|---|---|
| 3,258,935 | A | 7/1966 | Ross |
| 4,406,762 | A | 9/1983 | Ray et al. |
| 6,345,509 | B1 | 2/2002 | Garlov et al. |
| 7,678,931 | B2 | 3/2010 | Fichtall et al. |
| 7,900,857 | B2 | 3/2011 | Medoff |
| 8,418,944 | B2 * | 4/2013 | Medoff ............. C08H 8/00 241/23 |
| 9,476,069 | B2 | 10/2016 | Medoff |
| 2004/0231342 | A1 | 11/2004 | Hong et al. |
| 2008/0020437 | A1 | 1/2008 | Savarese |
| 2009/0117635 | A1 | 5/2009 | Bradley et al. |
| 2009/0286295 | A1 | 11/2009 | Medoff |
| 2009/0314487 | A1 | 12/2009 | Medoff |
| 2009/0321026 | A1 | 12/2009 | Medoff |
| 2010/0000853 | A1 | 1/2010 | Medoff |

FOREIGN PATENT DOCUMENTS

| | | |
|---|---|---|
| CN | 101517086 A | 8/2009 |
| CN | 101778949 | 7/2010 |
| CN | 102770546 | 11/2012 |
| JP | S60244337 | 12/1985 |
| JP | S61078390 | 4/1986 |
| JP | 2004261696 | 9/2004 |
| JP | 2005508748 | 4/2005 |
| JP | 6294949 B2 | 3/2018 |
| KR | 10-2009-0046851 | 5/2009 |
| RU | 2159816 | 11/2000 |
| WO | 200078446 | 12/2000 |
| WO | 2006009252 | 1/2006 |
| WO | 2006047445 | 5/2006 |
| WO | 2008011598 | 1/2008 |
| WO | 2008073186 | 6/2008 |
| WO | 2009001985 | 12/2008 |
| WO | 2009023443 | 2/2009 |
| WO | 2009134745 | 11/2009 |
| WO | 2009134764 | 11/2009 |
| WO | 2009134816 | 11/2009 |
| WO | 2009140057 | 11/2009 |
| WO | 2010/009240 | 1/2010 |
| WO | 2009134791 | 1/2010 |
| WO | 2011087965 | 7/2011 |

OTHER PUBLICATIONS

Liang et al., "Effect of Pretreatment Methods on Biotransformation of Crop Straw", Shanxi Food Industry, 4th Issue, Dec. 2004, 4 pages.
English translation of Vietnamese Patent Application No. 1-2012-02004 Office Action dated Jun. 28, 2018.
Chilba (http:/www.ag.auburn.edu/~chibale/an03microbiology.pdf), accessed Feb. 4, 2013.
Japanese Office Action—Japanese Corresponding Application No. 2012-548983, dated Feb. 24, 2015, 3 pages.
Mason, T.K., "Mobile Biomass Pelletizing System", Bonfire Biomass Conversions LLC, Published Apr. 14, 2009, pp. 1-15.
Office Action—Corresponding Australian Patent Application No. 2014262184, dated Sep. 25, 2015, 9 pages.
Office Action—Corresponding Japanese Application No. 2012-0548983, dated Sep. 20, 2016, 6 pages [no translation].
Office Action dated Apr. 4, 2017 issued by the Japan Patent Office in corresponding JP Patent Application No. 2015-208256 (7 pages).
Office Action dated Feb. 21, 2017 issued by the European Patent Office in corresponding EP Application No. 11733221.3 (6 pages).
Office Action dated Jan. 11, 2017 issued by the Korean Intellectual Property Office in corresponding KR Application No. 10-2012-7018464 (8 pages).

(Continued)

*Primary Examiner* — Ruth A Davis
(74) *Attorney, Agent, or Firm* — Leber IP Law; Celia H. Leber (57) ABSTRACT

Systems and methods for cooling and processing materials are disclosed.

7 Claims, 2 Drawing Sheets

(56) References Cited

OTHER PUBLICATIONS

Office Action dated Mar. 13, 2017 issued by the State Intellectual Property Office of China in corresponding CN Application No. 2014104590972 (1 page).
English translation of Search Report—Corresponding Chinese Application No. 2014102704589, dated Jun. 24, 2016, 2 pages.
Search Report—Corresponding PCT Application No. PCT/US11/020583, dated Jan. 7, 2011.
Stevens, R.W. (On the Stowage of Ships of their Cargoes, Freights, Charter-Parties, etc. Jan. 1859, Longman, pp. 57-58).
Decision to Grant—Corresponding Japanese Application No. 2016-244473, dated Feb. 6, 2018, 2 pages.
Examination Report—Corresponding Indian Application No. 1531/MUMNP/2012, dated Jan. 22, 2018, 7 pages.

* cited by examiner

A # COOLING AND PROCESSING MATERIALS

RELATED APPLICATIONS

This application is a continuation of U.S. patent application Ser. No. 15/586,159, filed May 3, 2017, which is a continuation of U.S. patent application Ser. No. 13/532,976, filed Jun. 26, 2012, now abandoned, which is a continuation of International Application No. PCT/US2011/020583, filed Jan. 7, 2011, which claimed priority to U.S. Provisional Application Ser. No. 61/295,476 filed Jan. 15, 2010. The complete disclosure of each of these applications is hereby incorporated by reference herein.

BACKGROUND

Biomass, particularly biomass waste, is abundantly available. It would be useful to derive materials and fuel, such as ethanol, from biomass.

It would also be useful to more efficiently process petroleum containing materials to obtain fuels and other products.

SUMMARY

The methods disclosed herein utilize cooling and processing of materials, alone or in combination with one or more with other processing techniques, to change the structure and thereby facilitate further processing of the materials. For example, in the case of biomass, cooling is used to reduce the recalcitrance of the biomass to facilitate processing of the biomass into a product such as a fuel. One or more of the steps of the methods disclosed herein may be performed in transit, e.g., by train, ship, barge, tanker truck or the like, and/or two or more steps of the method may be performed at different locations. In some implementations, the equipment that is used to perform one or more steps of the process is portable, e.g., to allow the processing equipment to be moved from one production site to another depending on availability of feedstocks and/or other resources. For example, the methods may include one or more of the mobile processing systems described in U.S. Ser. No. 12/374,549, the full disclosure of which is incorporated herein by reference.

By cooling the biomass or other material, the brittleness of various components of the biomass or other material (e.g., hemicellulose and/or lignin and/or proteins and/or pectin and/or minerals) can be increased, thereby significantly improving the effectiveness of the processing techniques that are used to alter the material. By increasing the brittleness of the materials, the materials can be fractured (e.g., the edges of fibers can be fractured) or cracked as a result of various processing steps. Fracturing can be, e.g., microfracturing.

In addition, cooling the material can have other effects that arise from differential rates of expansion and/or contraction of various components of the material. For example, certain components (e.g., lignin with water present) can contract or expand at faster rates than, or in different amounts than other components (e.g., hemicellulose, cellulose) with which they are associated. As a result, the subject material can be weakened, promoting modification, restructuring, and/or separation (e.g., phase separation, delamination, interfacial cleavage, cracking, or fracturing, e.g., microfracturing) of its various components. These processes—which can occur independently of other processing techniques or in conjunction with other processing techniques—can also improve yields of products, e.g., ethanol and or butanol, obtained from hemicellulose or cellulose. Cooling reduces the recalcitrance of the material, facilitating conversion of the cellulosic components of the material into a sugar solution (saccharification of the cellulose by an enzyme). Without wishing to be bound by theory, it is believed that the fracturing of the material can allow the enzyme to penetrate the material at the fracture sites, thereby accelerating saccharification. The saccharified material can then be converted to a product, e.g., fermented to ethanol and/or butanol.

When cooling is combined with other processing techniques, e.g., radiation and/or oxidation, the other techniques can be used to a lesser extent to obtain equivalent results. For example, when cooling is used with radiation the radiation can be used at a lower dose to provide the same degree of reduction in recalcitrance. Other processing techniques may include, e.g., grinding, milling, agitating, abrading, chopping, shearing, water knifing, gas knifing, steam knifing, one or more radiation processing steps (e.g., exposure to charged particles such as electrons and/or ions), one or more sonication processing steps, one or more chemical processing steps (e.g., using agents such as acids, bases, oxidizing agents, reducing agents, and/or solvents), and/or one or more thermal processing steps (e.g., pyrolysis, in the presence of oxidizing and/or other agents, and/or in reduced pressure environments). These other processing techniques, if used, can be performed before, during or after cooling.

During the various processing techniques that are used to alter and/or convert materials into other materials, a significant amount of heat can be generated in the materials. To avoid combusting or otherwise initiating unwanted thermal alteration of the materials, the cooling methods disclosed herein can be used to dissipate or offset the excess heat. The extent of cooling (e.g., the amount of heat removed from the material) can be varied according to the amount of heat generated during processing of the material. The extent of cooling can also be adjusted to adjust certain properties of the biomass material, such as its brittleness, to improve the efficiency of certain subsequent processing steps. For example, communution of the hemicellulose, cellulose, and lignin, and separation of these components can be enhanced by the methods disclosed herein.

The cooling and processing methods can also be used to treat other types of materials such as hydrocarbon-containing materials (e.g., petroleum-containing material). Various types of petroleum-containing materials—including, for example, heavy and light crude oils, natural gas, oil sands, oil shale, tar sands, bitumen, coal, and/or various hydrocarbon blends—can be cooled and processed using the methods disclosed herein to promote extraction, cracking, communution, separation, and refining of various components of the material, and to regulate temperature during refining, conversion, and purification processes such as cracking, reformation (catalytic and non-catalytic), distillation, and catalytic conversion.

As used herein, a "cryogenic" material is a material at a temperature of 200 K or less (e.g., 170 K or less, 150 K or less, 130 K or less, 120 K or less, 110 K or less, 100 K or less, 90 K or less, 80 K or less, 70 K or less, 60 K or less, 50 K or less, 40 K or less, 30 K or less). Thus, for example, a "cryogenic liquid" is a liquid having a temperature of 200 K or less.

As will be discussed in further detail below, various materials can be used for cooling, including for example liquid nitrogen, carbon dioxide, and ice.

The methods disclosed herein can produce material particles (e.g., fibers) having a length-to-diameter ratio of 5:1 or more (e.g., 6:1 or more, 8:1 or more, 10:1 or more, 12:1 or more 15:1 or more, 20:1 or more).

The methods disclosed herein can also produce particles having a largest dimension, e.g., diameter, of less than, e.g., 2000 nm, 1000, 750, 500, 250, 100, 50, 25, 20, 10, 5, or even 1 nm.

The methods disclosed herein can produce materials having a reduced bulk density. For example, the bulk density of the materials produced using the methods disclosed herein can be 0.8 g/cm$^3$ or less (e.g., 0.6, 0.5, 0.4, 0.3, 0.2 or less, e.g., 0.1 g/cm$^3$).

The methods disclosed herein can produce materials having relatively thin cross-sections, due to the combined effects of cooling the material to increase its brittleness, and processing the material using any one or more of the techniques disclosed herein. In general, materials having thin cross-sections can be cooled more efficiently than materials having thicker cross-sections; as a result, the costs (e.g., energy consumption) for material processing (e.g., particularly the costs for energy consumption in processing techniques) can be reduced.

In one aspect, the invention features a method that includes converting a cooled biomass material to a product utilizing a microorganism and/or enzyme, wherein at least one of cooling and converting the biomass material is performed using a mobile processing unit.

Some implementations include one or more of the following features. The biomass material may have been treated by grinding or comminuting the biomass material, e.g., before, during or after cooling. The biomass material can be irradiated, e.g., before, during, or after cooling. Comminuting can be performed in a freeze grinding or freeze milling device. The product can be, for example, an alcohol, e.g., ethanol and/or butanol. The biomass material can be or include a cellulosic or lignocellulosic material.

In some cases, the biomass material includes cellulose and converting the cooled material includes utilizing an enzyme to saccharify the cellulose. In such cases, the method can further include fermenting the product of saccharification to produce an alcohol.

The invention also features similar methods in which the feedstock comprises a hydrocarbon-containing material. For example, in one aspect the invention features a method that includes converting a cooled hydrocarbon-containing material to a product utilizing a microorganism and/or enzyme, wherein at least one of cooling and converting the material is performed using a mobile processing unit.

The invention also features products formed by any of the methods described herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

This application incorporates by reference herein the entire contents of each of the following applications: U.S. Ser. Nos. 12/374,549, 12/417,699, 12/417,707, 12/417,720, 12/417,723, 12/417,731, 12/417,786, 12/417,840, 12/417,880, 12/417,900, 12/417,904, 12/429,045, 12/486,436, and 12/502,629, and U.S. Provisional Application No. 61/151.695.

Other features and advantages will be apparent from the description, drawings, and claims.

DETAILED DESCRIPTION

In some cases, the processes described herein are used to convert a cellulosic or lignocellulosic feedstock to a convenient and concentrated form which can be easily transported and utilized, e.g., in a manufacturing facility, for example a plant adapted to manufacture ethanol. In such cases, the process includes saccharification of the feedstock, and transportation of the feedstock from a remote location, e.g., where the feedstock is produced or stored, to the manufacturing facility. In some cases, saccharification can take place partially or entirely during transport. To facilitate saccharification, the process further includes reducing the recalcitrance of the feedstock, before or during saccharification, by cooling the material as will be described in detail below.

In some embodiments, cooling takes place at a first location, or during transit (e.g., in a rail car or truck or on a barge or ship), and saccharification and/or other further processing (such as fermentation) takes place at one or more other locations. In some cases, cooling of the material takes place in transit due to the cold ambient conditions under which the material is transported. e.g., sub-freezing ambient temperatures.

In some embodiments, the equipment used for cooling and/or for further processing steps is mobile and is transported from one manufacturing site to another, e.g., based on the availability of feedstock.

Some of these systems eliminate or at least reduce the need for transporting the starting material, e.g., biomass, which is often of a low bulk density, to a stationary large-scale production facility. It also may reduce the need to transport the desired product produced by the mobile facility a long distance to its end user or a distribution facility.

Mobile Processing

Mobile facilities may be used to perform one or more of the method steps described herein. Transporting the production facility or components of the facility rather than the biomass starting material is particularly useful and economical given that many of the feedstocks used to produce energy (e.g., bioethanol, gasoline, hydrogen, natural gas) or other desired products may be seasonal or otherwise only periodically available. Therefore, a production facility only needs to be operational in the area when the feedstock or other biomass is available for processing. After the processing is done, the facility or certain components of the facility can travel to another area with feedstock or other biomass available for conversion to a desired product.

The facilities or components thereof may be transported by water, air, land, or any combination thereof. For example, the production facility or components thereof may be transportable on a boat, barge, ship, or other nautical vessel. Such facilities are particularly useful for producing ethanol, butanol, or other products from aquatic biomass such as algae (e.g., Sargassum) or aquatic plants. These facilities are also useful in traveling on a body of water to different areas with biomass suitable for the production of the desired product (e.g., traveling on a river or on the ocean and docking at an area with suitable biomass for processing). The mobile facilities or components thereof may also be transported on land. For example, the facility may be transported by a car, a truck, tractor trailer, and railroad car(s). Again, the land vehicle with the portable facility can travel to areas with biomass suitable for the production of the desired product. Finally, the facilities may be transported by air. The facility may be transported by plane, helicopter, and blimp. Air transportation of the facility allows for the use of biomass typically too far away from production facilities to be used. The facility may be on the plane, or the facility or components may be dropped from a plane or delivered by plane. The mobile facility is typically conveniently sized and organized to provide for easy transportation of the facility and/or its individual components. In the case of land transport, the transportation vehicles are typically able to travel roads and highways used by cars, trucks, and tractor trailers. In the case of sea transport, the facility or components are typically carried by a boat or barge which is moved by a boat. In the case of air transport, the facility or components is sized to fit in a plane (e.g., cargo plane) or helicopter.

The mobile facilities or facilities constructed from mobile components may include any or all of the following apparatuses useful in producing the desired product (e.g., ethanol or butanol): equipment for pre-processing the biomass (e.g., with cooling and/or other treatments such as radiation), mills, cookers, cooling containers, holding containers, fermenters, distillation apparatuses, columns, piping transfer containers, and mixing containers. In certain embodiments, the different stages of the production facilities are linked together efficiently so that a user can easily transfer materials from one stage of the production process to another. The facilities may also include any reagents needed in the production process including yeast or other microorganisms (including genetically engineered microorganisms), enzymes (e.g., amylase, and cellulase), acids (e.g., sulfuric acid, hydrochloric acid), bases (e.g., sodium hydroxide), chemical reagents, water, salts, molecular sieves, and columns. In certain embodiments, when ethanol is being produced, the facility includes denaturants such as gasoline or other alcohols for denaturing the ethanol. The facilities can include all the necessary equipment and reagents conveniently stored in the facility making for easy use of the facility.

In certain embodiments, the facility produces enough ethanol, butanol, or other energy source to supply the energy needs of a factory, town, village, and island. In certain embodiments, the production facility produces less than 5 million gallons of ethanol or butanol per year. The facility may also optionally include any equipment mandated by international, federal, state, or local law including, for example, safety equipment necessary to prevent or handle spills, fires, or other emergencies.

The production facility may be assembled from various transportable components. The facility may include non-transportable components. The components are preferably designed for easy assembly of the working facility at the site. The components may be pre-fabricated. The components may be interchangeable and may provide for scalability of the facility. In certain cases, the component system allows the facility to be easily assembled and broken apart for ease of portability. The various components of the facility may be brought to the site using any combination of transport means (e.g., air, water, and land). In certain embodiments, the components are brought to a site with certain infrastructure which may include electricity, shelter, foundation, sewer, water, and natural gas lines. All or some of the components may be later disassembled and moved to a new site. In certain embodiments, particular components and/or the infrastructure may remain at the site to be optionally used again.

In some embodiments, the facility or components thereof are meant to be transported from place to place with suitable biomass. The facility may be completely self-sufficient requiring only the addition of biomass, or the facility may require other materials or utilities such as water, electricity, natural gas, gasoline, and sewer. For example, the ethanol, butanol, or other energy produced by the mobile facility may be used to power a generator to supply electricity to the facility, or the ethanol, butanol, or other energy source may be burned to provide the heat to break down the biomass in a cooker or to run a distillation. The ethanol, butanol or other energy source may also be used to power the vehicle used to transport the facility or components thereof.

The facility may be a small-scale production facility (e.g., producing less than 5 million gallons, or less than 1 million gallons.) These small-scale facilities may include a module for cooling the material, or cooling may be performed at a different location or in transit. In certain embodiments, the facility produces enough fuel to supply the needs of a factory, town, village, and island. In certain embodiments, the facility produces less than 5 million gallons per year.

In some cases, the process uses biomass from a local area in a small scale and/or mobile production facility to produce a desired product locally. The locally produced product (e.g., ethanol, butanol, gasoline, natural gas, hydrogen gas, and hydrocarbons) is then preferably used locally to avoid the cost of the transporting both the biomass and the final product. Preferably, a local water source is used in the production process. Other reagents needed for the process may be provided by the facility or provided locally. The waste or co-products from the production process, e.g., the distillers grain, can be used locally as a highly nutritious livestock feed or as a fertilizer. Other waste products or co-products from the process such as biomolecules, carbohydrates, protein, and polymers may also be packaged, used, and/or sold. The mobile component-based production facilities and small-scale production facilities complement larger-scale production facilities (i.e., facilities that produce over 10-20 million gallons of ethanol per year). In some cases, the inventive facilities may eliminate the need for large-scale production facilities in some areas. The portable nature of certain systems works especially well given the cyclical nature of crops and other biomass in various geographic areas. These inventive facilities also allow for the economical production of ethanol and/or other fuels from low cost biomass, which will aid, for example, in making ethanol a competitive fuel additive.

Further details of mobile processing are disclosed in U.S. Ser. No. 12/374,549, the disclosure of which was incorporated by reference hereinabove.

Cooling

The methods disclosed herein use cooling techniques, e.g., cryogenic cooling techniques, for example to ensure that undesired thermal decomposition, e.g., of cellulose and/or hemicellulose, does not occur during material processing. Cooling can also be used to modify properties of the material and facilitate conversion of the material by reducing the recalcitrance of the material.

In particular, the cooling methods disclosed herein can be used alone or in combination to increase the brittleness of materials, making the cooled materials more amenable to modification via one or more processing methods such as one or more processing steps (e.g., grinding, cracking, shattering, compressing, milling, agitating, abrading, chopping, shearing), one or more radiation processing steps (e.g., exposure to charged particles such as electrons and/or ions), one or more sonication processing steps, one or more chemical processing steps (e.g., using agents such as acids, bases, oxidizing agents, reducing agents, and/or solvents), and/or one or more thermal processing steps (e.g., pyrolysis, in the presence of oxidizing and/or other agents, and/or in reduced pressure environments). By increasing the brittleness of the material by cooling and improving the efficiency with which the material by cooling can be processed, e.g., by communution or separation, processing costs (e.g., energy-related processing costs) can be reduced and intended product yields can be increased.

Moreover, when a multi-component material is cooled, different components thereof will contract and/or expand at different rates and/or in different amounts. In certain embodiments, this process can lead to breakage of chemical bonds in the material. For example, this cooling behavior can introduce stresses between bound components, leading to processes such as delamination, fracturing, peeling, disassociation, and separation of the bound components. As a result, the efficiency with which the components can be separated—and the yields of various intended products derived from the material—can be increased or decreased or kept in balance.

Cooling, alone or in combination with other treatments such as irradiation and/or oxidation, can be used to control the functionalization of the fibrous material, i.e., the functional groups that are present on or within the material. The functionalization of the material can increase solubility and/or dispersibility and can make the material more susceptible to conversion by enzymes and/or microorganisms.

The temperature to which the material is cooled depends upon a number of factors, including the processing techniques that are used to alter the material and the nature of the material. In some embodiments, for example, the material is cooled to a temperature less than the glass transition temperature of lignin, which is about 100° to 170° C., e.g., about 120° to 150° C., e.g., about 125° C. When the lignin is cooled below its glass transition temperature, it changes from a soft, deformable material to a brittle, glassy material. The brittle, glassy lignin can be more readily altered by various processes, including the processes disclosed above. Further, by cooling the lignin below its glass transition temperature the physical structure of the lignin can be changed. Changes to the lignin structure can lead to internal stresses within the material where the lignin is bound to cellulose and/or hemicellulose. These internal stresses can lead to delamination and thus separation of the lignin from the cellulose and/or hemicellulose. In some implementations, the material is cooled below the temperature at which the material becomes brittle (the "brittle point" of the material). This brittle point of a particular material can be measured using commercially available testing equipment, e.g., the Benz BPT2100 Brittlepoint Tester available from Benz Material Testing Instruments, Providence, R.I.

In some embodiments, the material can be cooled below a glass transition temperature of one or more other elements or components in the material, such as hemicellulose. Similar considerations to those that are discussed above in connection with lignin apply to hemicellulose as well. In particular, cooling of the hemicellulose can make it more brittle, improving the efficiency of subsequent processing steps. Cooling can also introduce internal stresses within the biomass structure, which can lead to separation of the hemicellulose from other components (e.g., cellulose) in the material.

The material can be cooled to a temperature of, for example, 400 K or less (e.g., 380 K or less, 360 K or less, 340 K or less, 320 K or less, 300 K or less, 280 K or less, 260 K or less, 240 K or less, 220 K or less, 200 K or less, 150 K or less, 100 K or less, 80 K or less, 77 K or less, 70 K or less, 50 K or less). In some embodiments, the material can be cooled to a temperature less than or equal to room temperature (e.g., 293 K). In certain embodiments, the material can be cooled to about the temperature of liquid nitrogen (e.g., 77 K) or less. Cooling the material to temperatures less than the temperature of liquid nitrogen can be achieved by using cooling fluids with a lower boiling point than liquid nitrogen (e.g., liquid helium).

The rate at which the material is cooled can be controlled to assist in separating components of the material. For example, by cooling the material rapidly, lowest-energy arrangements of the associated components in the biomass may not have time to form. In other words, the cooled material may be in an energy state that is not a minimum energy state, and can therefore be unstable and more readily altered using further processing steps. In certain embodiments, for example, the rate at which the material is cooled is 1 K/s or more (e.g., 2 K/s or more, 3 K/s or more, 5 K/s or more, 7.5 K/s or more, 10 K/s or more, 15 K/s or more, 20 K/s or more, 30 K/s or more, 40 K/s or more, 50 K/s or more, 75 K/s or more, 100 K/s or more, or even more).

The material can be maintained at a selected temperature and/or within a selected temperature range during processing of the material using any one or more of the various processing techniques disclosed herein. For example, the material can be maintained at a temperature of 400 K or less (e.g., 380 K or less, 360 K or less, 340 K or less, 320 K or less, 300 K or less, 280 K or less, 260 K or less, 240 K or less, 220 K or less, 200 K or less, 150 K or less, 100 K or less, 80 K or less, 77 K or less, 70 K or less, 50 K or less). In some embodiments, the material can be maintained at or below room temperature (e.g., 293 K). In certain embodiments, the biomass can be maintained at the temperature of liquid nitrogen (e.g., 77 K) or less.

In certain embodiments, the material can be subjected to a sequence of heating and cooling stages that are selected to cause further disruption to the association (e.g., suspected covalent bonds) between lignin and cellulose and/or hemicellulose. Rapid thermal cycling of the material can introduce internal stresses within the material, which can lead to separation of biomass components (e.g., without further processing, or as a result of further processing steps).

In some embodiments, multiple different cooling stages can be used, each of which is configured to cool the material to a different temperature. For example, in an initial stage of processing, the material can be cooled to a selected temperature and can be processed (e.g., mechanically, with radiation exposure, with sonication, and/or with various other techniques). For example, in each subsequent stage of processing, as the material particles can be made increasingly smaller, the material can be cooled to successively lower temperatures and further processed, to continue to reduce the size of the particles and/or further disassociate components of the material such as biomass (e.g., disassociate lignin from cellulose and/or hemicellulose) or to change the structure.

In some cases, cooling can be performed by leaving the material outdoors or in an unheated building or enclosure in a cold climate (e.g., where the average ambient temperature during the cooling period is less than 0° C., less than −5° C., −10° C., or even less than −15° C.), or can be performed while the material is in transit, e.g., on a train, barge or ship.

Further details of cooling treatments are described in U.S. Ser. No. 12/502,629, the disclosure of which was incorporated by reference hereinabove.

Processing Systems

Figure 1:
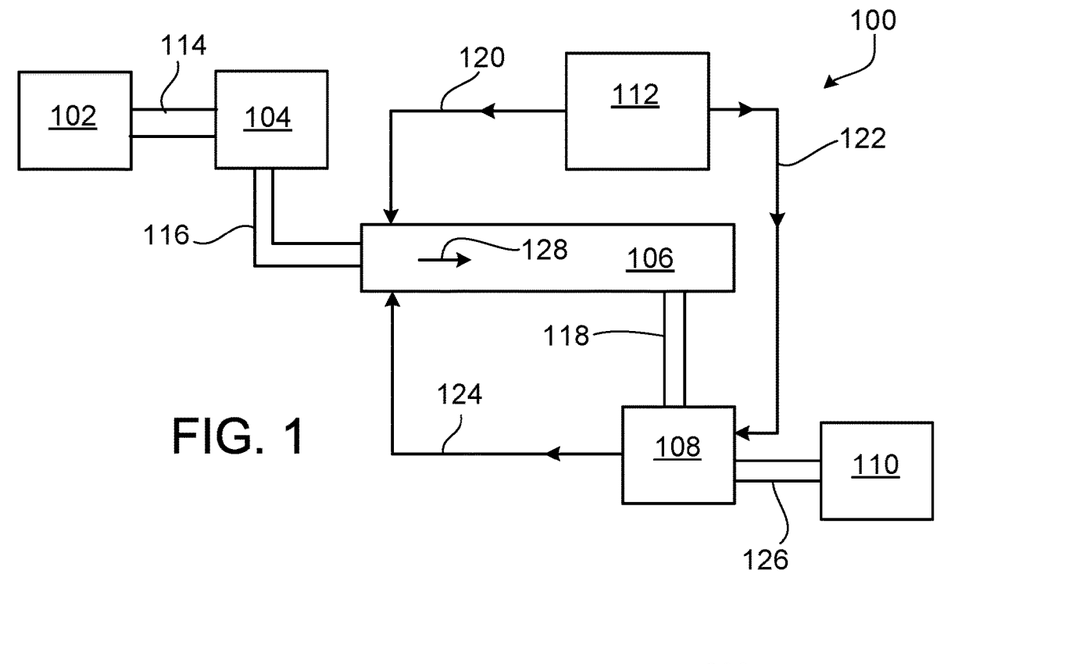
FIG. 1 is a schematic diagram showing a biomass processing system.
Figure 2:
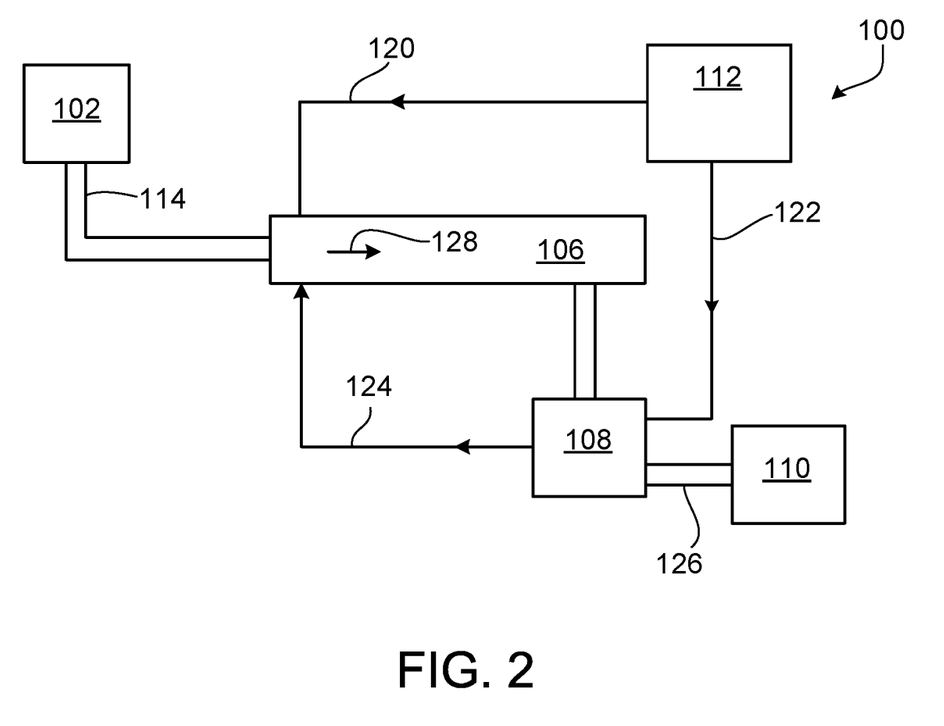
FIG. 2 is a schematic diagram showing a biomass processing system.
Figure 3:
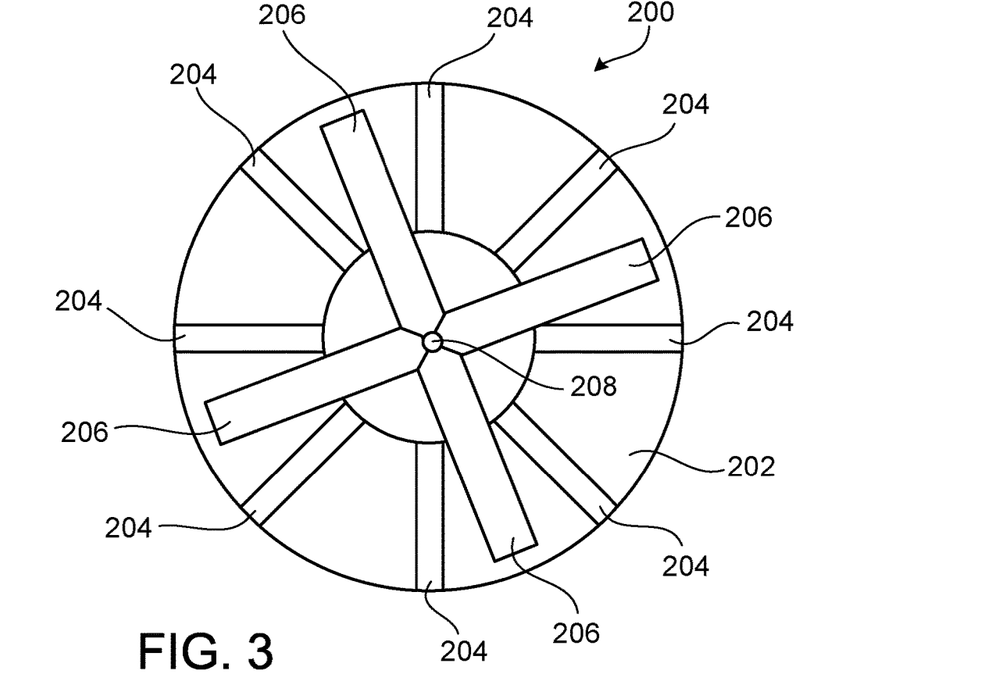
FIG. 3 is a schematic diagram showing a milling unit.

Examples of processing systems for use in the methods described herein are shown in FIGS. 1-3 and described below. In these systems, one or more components of the system, or the system as a whole, can be mobile. Moreover, one or more of the components can be located remotely from one or more other components of the system.

FIG. 1 shows a schematic diagram of a biomass processing system 100. System 100 includes a material storage unit 102, a first material processing sub-system 104, a cooling conduit 106, a second material processing sub-system 108, a processed material reservoir 110, and a cooling fluid supply unit 112. During operation, material stored in storage unit 102 is transported via conduit 114 to first material processing sub-system 104.

Sub-system 104 can include a variety of different processing units. For example, in some embodiments, sub-system 104 can include one or more mechanical processing units (e.g., grinding units, agitation units, milling units, abrasion units, chopping units, shearing units). In certain embodiments, sub-system 104 can include one or more radiation processing units. The radiation processing units can include charged particle sources (e.g., electron beam sources and/or ion sources), in which the material is exposed to charged particles to cause alteration of the material. In some embodiments, sub-system 104 can include one or more sonication units, in which material is exposed to ultrasonic waves to alter the material. In certain embodiments, sub-system 104 can include one or more pyrolysis units and/or one or more chemical processing units. In some embodiments, sub-system 104 can include one or more steam explosion processing units. In some embodiments, sub-system 104 can include one or more combinations of these processing units.

In general, sub-system 104 can include any one or more of the above processing units, in any combination. Sub-system 104 is generally configured to provide an initial stage of alteration of the material, in preparation for further processing steps. In some embodiments, sub-system 104 may not be present at all, and material may be transferred directly from storage unit 102 to cooling conduit 106. FIG. 2 shows an embodiment of a material processing system that does not include a processing sub-system 104. The various components in FIG. 2 have been discussed above in connection with FIG. 1, and their descriptions are not repeated at this point.

Referring again to FIG. 1, after the material has been processed in sub-system 104, e.g., by cutting, chopping, shearing, or shredding, the material is transferred via conduit 116 to cooling conduit 106. Cooling fluid supply unit 112 supplies cooling fluid (e.g., liquid nitrogen and/or cooled nitrogen gas, and/or liquid helium and/or cooled helium gas, and/or liquid argon and/or cooled argon gas, and/or solid $CO_2$ and/or liquid $CO_2$, and/or liquid air and/or cooled gaseous air) to cooling conduit 106 via conduit 120. The material is transported through cooling conduit 106 in the direction shown by arrow 128. As the material moves through conduit 106 (e.g., on a transport device such as a conveyor belt and/or an auger), the material is cooled via heat exchange with cooling fluid supplied by cooling fluid supply unit 112.

When the material reaches the end of cooling conduit 106, the material is transported through conduit 118 to second material processing sub-system 108. In some embodiments, cooling fluid supply unit 112 supplies cooling fluid via conduit 122 to second sub-system 108, as shown in FIG. 1. In general, second processing sub-system 108 can include one or more of any of the processing units disclosed herein in connection with first processing sub-system 104. Exemplary processing units include one or more processing units such as grinding, chopping, or shearing units, radiation processing units, sonication processing units, pyrolysis processing units, steam explosion processing units, and chemical processing units. Cooling fluid can be recycled for further use in cooling conduit 106 by transporting the fluid via conduit 124.

The processed material, after emerging from second processing sub-system 108, is transported to material reservoir 110 through conduit 126. Once in reservoir 110, the material can be subjected to further processing steps, including any one or more additional steps from among those disclosed in connection with processing sub-systems 104 and 108 above. Alternatively, or in addition, the processed material can be subjected to additional processing steps, including one or more processes using biological agents such as enzymes and/or microorganisms, such as bacteria and/or yeast and various chemicals and chemical formulations and solutions.

In some embodiments, the material is comminuted, e.g., milled or ground, during cooling. For example, FIG. 3 shows an exemplary embodiment of a milling unit 200 that can form a portion of either or both of processing sub-systems 104 and 108. Milling unit 200 includes a conduit 202 through which material is transported. Fixed blades 204 are positioned within the conduit. Rotating blades 206 are attached to a centrally positioned shaft 208. During operation, the material is milled through the cutting action of blades 204 and 206.

Commercially available freeze milling, freeze grinding, cryomilling and cryogrinding equipment may be used. Such equipment combines cooling of the material with comminution of the material. Examples of commercially available cryogrinding devices include the Freezer/Mill 6870, available from SPEX CertiPrep, Metuchen, N.J., and the cryogenic grinding devices available from Pulva Corporation, Saxonburg, Pa. Other suppliers include Air Products, Praxair, and Air Liquide. In some embodiments, the equipment may include a pre-cooling area, e.g., a cooling conveyor such as a cooled screw extruder. In some cases liquid nitrogen is sprayed onto the material to be cooled in the pre-cooling area. The grinding may be provided, for example, by a reciprocating pin or other element. For example, the grinding device may be a pin mill. It is generally preferred that the temperature of the material be monitored and controlled throughout feeding and grinding.

Freeze grinding may be combined with irradiation, in which case irradiation can be performed before, during, or after freeze grinding. In some cases, freeze grinding can reduce the amount of radiation that is needed to reduce the recalcitrance of a biomass material or process a hydrocarbon-containing material.

Other Processing Steps

In general, the cooling methods disclosed herein can be used with a wide variety of different biomass and other material processing techniques. Exemplary techniques that can be used with the cooling methods discussed herein are disclosed, for example, in the following patent applications: WO 2008/073186; and U.S. Ser. Nos. 12/417,699, 12/417,707, 12/417,720, 12/417,723, 12/417,731, 12/417,786, 12/417,840, 12/417,880, 12/417,900, 12/417,904, 12/429,045, and 12/486,436. The disclosed cooling methods can generally be used before, during, and/or after any of the processing techniques described above are implemented.

Sonication processing techniques can, in certain embodiments, be particularly advantageous when used in combination with, e.g., before, immediately after, or during, the cooling methods disclosed herein. In general, sonication processing of material is effective at altering the material due to heat supplied to the material via mechanical waves (e.g., sound waves). When cooling methods are used to reduce the temperature of the material, the material becomes more brittle, and is less able to deform in response to incident mechanical waves and/or undergo rapid expansion due to local heating. As a result, the efficiency with which sonication effectively changes the material is increased.

In some embodiments, techniques that use radiation (e.g., electron beams and/or ion beams) to process material can be particularly advantageous when used in combination with, e.g., before, immediately after, or during, cooling of the material. For example, in certain embodiments, material can first be irradiated (e.g., in sub-system 104) before it is cooled. Alternatively, the material can first be cooled, and then irradiated (e.g., in sub-system 108). The radiation dose may be, for example, from about 0.1 MRad to 200 MRad, e.g., from about 10 MRad to 100 MRad or about 30 MRad to 90 MRad. The radiation may be delivered in a single irradiation step or multiple irradiation steps, and the material can be cooled between irradiation steps if desired. Such cooling is described in U.S. Ser. No. 12/417,880.

Exposure of the material to certain types and dosages of radiation may increase the brittleness of the material. The material can be cooled to decrease its temperature and further increase its brittleness. During and/or after the cooling of the material, the material can be processed (e.g., via milling, grinding, shearing, and other such techniques) to alter the material in preparation for further processing steps that produce useful products. Alternatively, or in addition, radiation exposure (e.g., electron beam exposure and/or ion beam exposure) of the material after cooling the material can also be used to further alter the material and/or make the material more brittle. When both radiation exposure and cooling are used to make the material more brittle, product yields (e.g., ethanol and/or other alcohols) can be significantly increased, and the amount of energy required to process the material can be reduced.

In certain embodiments, multiple cooling and mechanical processing stages, or alternating cooling and heating stages, e.g., with our without additional mechanical or other physical processing, can be used to process a material, e.g., biomass. For example, each successive stage can further reduce the average size of the biomass particles, until a desired particle size is reached. Each cooling stage can be similar or different (e.g., the system can include a plurality of similar cooling sub-systems). In some embodiments, the system can include a single cooling sub-system through which the material passes multiple times. Alternatively, in certain embodiments, different cooling stages (e.g., cooling stages that cool the biomass to different temperatures, such as progressively lower temperatures) can be used to process the material.

Similarly, in certain embodiments, multiple mechanical processing stages can be used to process biomass or other materials such as petroleum products. The materials can be recirculated through the same processing unit multiple times, and/or the system can include multiple mechanical units. The units can all be similar to one another, or some of the units can differ (e.g., in structure) from one another.

In general, a wide variety of different cooling fluids can be used to cool the material. In the embodiments discussed above, liquid and/or cold gaseous nitrogen was used as the cooling fluid. However, in some embodiments, one or more other cooling fluids can be used, including liquid helium, liquid oxygen, liquid hydrogen, liquid air, other such fluids, and combinations thereof. In certain embodiments, the fluids can be gases rather than liquids, or can include solids (e.g., ice, solid $CO_2$) mixed with, or instead of, the liquids. For example, a wide variety of cooled gases (including cooled noble gases, cooled nitrogen gas, cooled oxygen gas, and cooled hydrogen gas) can be used in place of, or together with, liquid cooling fluids.

In certain embodiments, solids can be added to the materials to assist in processing the materials. For example, solid $CO_2$ can be added to the materials to assist in altering the materials in one or more processing units. Other solids that could also be used include ice, for example. The solid may also be a solid element that is later removed or separated from the material, e.g., one or more balls, pins, or other solid milling elements.

Optionally, the processing systems disclosed herein can include a separation sub-system that functions to separate various components of the material after the material has been cooled and processed. For example, when material is processed to disassociate lignin from cellulose and/or hemicellulose, the processing system can include a separation sub-system configured to remove the disassociated lignin. Various methods, including physical separation methods such as decanting, centrifuging, distillation, and extraction can be used to separate the components, e.g., the lignin from the other components of a lignocellulosic material, or sand from hydrocarbons in an oil sand. Other methods which can be implemented in the separation sub-system include thermochemical processing, chemical processing, and radiation exposure processing).

The processing systems disclosed herein can optionally include one or more wetting stations to introduce various wetting agents—particularly water and/or other liquids such as dimethyl sulfoxide—into the materials. For example, following mechanical processing units such as the milling unit shown in FIG. 3, the processing system can include a sprayer that adds water and/or other agents to the material. The sprayer can create a fine mist that settles on surfaces of the material's particles. If the material is cooled during or after the mist is applied, the mist can be frozen onto the surfaces of the particles to ensure adhesion. The temperature of the material can undergo one or more heating-cooling cycles to further swell the material with the applied mist. Further, in certain embodiments, changes, e.g., rapid changes, in the temperature of the material can further alter the material structure.

In some embodiments, multiple wetting stages can be used. Each of the multiple wetting stages can introduce the same agent into the material, or different stages can introduce different agents. The selection of which agents to introduce depends upon factors such as the intended application of the material, the physical-chemical state of the material, and the conditions in subsequent material processing stages.

Systems and methods for enhancing wetting of materials before, during, and after processing are disclosed, for example, in U.S. Ser. No. 12/417,880, the disclosure of which is incorporated herein by reference.

In some embodiments, after the materials have been processed using the methods disclosed herein, the processed materials can be contacted with biological agents such as enzymes, and/or with microorganisms such as yeast (e.g., *P. Stipitis*) and/or bacteria to extract a variety of useful products from the processed materials, including products such as hydrogen, alcohols (e.g., ethanol and/or butanol), organic acids (e.g., acetic acid), hydrocarbons, co-products (e.g., proteins) or mixtures of any of these. Suitable biological agents and microorganisms for further processing of materials are disclosed, for example, in U.S. Ser. No. 12/429,045, which was incorporated by reference hereinabove.

For example, as mentioned above, in some embodiments the techniques described herein are used to separate and remove lignin from a lignocellulosic material, and then the remaining cellulosic components are saccharified, e.g., using an enzyme. The removal of the lignin reduces the recalcitrance of the material, allowing the conversion of the cellulose to sugars, which can then be fermented to produce alcohols.

Materials

Examples of biomass materials can include any biomass material that is or includes carbohydrates composed entirely of one or more saccharide units or that include one or more saccharide units can be processed by any of the methods described herein. For example, the feedstock or biomass material can be cellulosic or lignocellulosic materials, starchy materials, such as kernels of corn, grains of rice or other foods, or materials that are or that include one or more low molecular weight sugars, such as sucrose or cellobiose.

For example, such feedstocks or biomass materials can include paper, paper products, wood, wood-related materials, particle board, grasses, rice hulls, bagasse, cotton, jute, hemp, flax, bamboo, sisal, abaca, straw, corn cobs, rice hulls, coconut hair, algae, seaweed, cotton, synthetic celluloses, or mixtures of any of these.

Biomass also includes cellulosic fiber sources, including paper and paper products (e.g., polycoated paper and Kraft paper), and lignocellulosic fiber sources, including wood, and wood-related materials, e.g., particle board. Still other biomass includes natural fiber sources, e.g., grasses, rice hulls, bagasse, cotton, jute, hemp, flax, bamboo, sisal, abaca, straw, corn cobs, rice hulls, coconut hair; fiber sources high in α-cellulose content, e.g., cotton; and synthetic fiber sources, e.g., extruded yarn (oriented yarn or un-oriented yarn). Natural or synthetic sources can be obtained from virgin scrap textile materials, e.g., remnants, or they can be post consumer waste, e.g., rags. When paper products are used, they can be virgin materials, e.g., scrap virgin materials, or they can be post-consumer waste. Aside from virgin raw materials, post-consumer, industrial (e.g., offal), and processing waste (e.g., effluent from paper processing) can also be used. Also, the fiber source can be obtained or derived from human (e.g., sewage), animal or plant wastes. Additional biomass sources have been described in U.S. Pat. Nos. 6,448,307, 6,258,876, 6,207,729, 5,973,035 and 5,952,105.

A variety of different agents can be added to the material prior to, during, and/or following cooling of the material. Exemplary agents that can be added include water (and, more generally, any other compounds that expand or contract when cooled), oxidizing agents, reducing agents, acids, bases, and materials that contract significantly upon cooling. In general, agents such as water can be introduced into one or more of the components of the material to cause swelling of the components when hydrated. For example, when the material, e.g., biomass, is cooled, the water expands and/or contracts, creating periodic internal stresses in the material that can lead to cleavage of bonds within the material, e.g., between lignin and cellulose and/or hemicellulose. Other agents that undergo sublimation (e.g., carbon dioxide) can also be used to produce similar results. Agents that sublime generally undergo significant changes in molar volume at a phase transition. Such agents can be introduced into the material to further promote separation of the components therein when relatively rapid expansion and/or contraction of the material occurs as a result of the added agents.

As noted above, various chemical agents such as oxidizing agents and/or reducing agents and/or acids and/or bases can be added to the material. The various agents can react with the material before, during, and/or after cooling to further assist in altering the material prior to product formation and extraction. In general, certain components of the material may be stable in the presence of one agent, but reactive in the presence of other agents. For example, cellulose is stable to bases, but is altered by acids. By introducing bases into one or more of the various processing sub-systems, one or more selected component(s) of the material, e.g., lignin, can be selectively altered and disassociated from other component(s), e.g., cellulose and/or hemicellulose, improving yields of products derived from the material. Chemical agents can be added to the various processing sub-systems as liquids, in solutions, and/or as gases. In some embodiments, the agents can be introduced in gaseous form, and can be condensed into liquids as the material is cooled.

In certain embodiments, various chemical oxidizing and/or reducing agents can be added before, during, and/or after cooling to promote separation of at least some of the material components via chemical reactions. Cooling alone, or together with one or more of the processing techniques disclosed above, can be used to promote modification, restructuring, and/or disassociation, e.g., of lignin from cellulose and/or hemicellulose. This modification, restructuring, and/or disassociation can be further promoted by reacting cellulose, hemicellulose, and/or lignin with agents such that the products of such reactions do not re-associate as readily. Exemplary oxidizing and reducing agents include ozone, oxygen, air, ammonia, and a wide variety of other agents.

Other Embodiments

The cooling and processing methods disclosed herein can also be used to treat other types of materials such as hydrocarbon-containing materials (e.g., petroleum-containing materials). Various types of petroleum-containing materials—including heavy and light crude oils, natural gas, oil sands, oil shale, tar sands, bitumen, coal, and/or various hydrocarbon blends—can be cooled and processed using the methods disclosed herein to promote separation of various components of the material, and to regulate temperature during refining, conversion, and purification processes such as cracking, reformation (catalytic and non-catalytic), distillation, and catalytic conversion, to improve the efficiency and to reduce the cost of such processes.

In some embodiments, the methods disclosed herein can be used to extract and/or separate hydrocarbon-containing materials from materials such as oil sands, oil shale, and tar sands. The methods can be used, for example, to separate petroleum-containing materials from sand, rock, and other inorganic and organic matter.

In the following sections, various petroleum processing steps are discussed; in general, cooling alone, or in combination with any of the processing techniques disclosed herein, can be used to improve the efficiency of these various processing steps.

Crude oils typically include large numbers of different hydrocarbon species, ranging from relatively light, volatile, low molecular weight hydrocarbons, to heavy, dense, highly viscous fractions (e.g., heavy oil, bitumen) of high molecular weight. The heavy crudes typically contain more sulfur and/or nitrogen and/or metals, relative to lighter, sweeter crudes such as the West Texas Intermediate, which is traded on the New York Mercantile Exchange. In general, sweet crudes include relatively low amounts of sulfur-containing compounds; the sour crudes include larger amounts of sulfur-containing compounds. Simple refineries are generally designed to handle sweet crudes, while more complex deep conversion refineries are required for the processing of heavy, sour crude oils.

The large number of different hydrocarbon (and other) species in crude oil typically establish a relatively delicately balanced colloidal solubility system. When certain properties of the crude oil are changed (e.g., temperature, pressure, and/or composition), the solubility balance can be destabilized, causing a single-phase crude oil feedstock to change to a multiphase, multicomponent mixture (which can include one or more gas, liquid, and solid phases). At room temperature and pressure, various components of crude oil are in different physical states. For example, lighter hydrocarbons (e.g., methane, ethane, propane, butane) are gases at room temperature and pressure. Components of intermediate molecular weight (e.g., pentane, hexane, octane, gasoline, kerosene, and diesel fuel) are liquids under these conditions. Heavy fractions (e.g., asphalt, wax) are solids at standard temperature and pressure. Due to this range of physical states, conventional refineries typically process crude oil at elevated temperatures and/or pressures to ensure that most (or all) of the hydrocarbon fractions in the crude are either liquids or gases Crude oil refining comprises processes that separate various hydrocarbon and other components in the oil and, in some cases, convert certain hydrocarbons to other hydrocarbon species via molecular rearrangement (e.g., chemical reactions that break bonds). In some embodiments, a first step in the refining process is a water washing step to remove soluble components such as salts from the crude oil. Typically, the washed crude oil is then directed to a furnace for preheating. As discussed above, the crude oil can include a large number of different components with different viscosities; some components may even be solid at room temperature. By heating the crude oil, the component mixture can be converted to a mixture that can be flowed from one processing system to another (and from one end of a processing system to the other) during refining.

Preheated crude is then sent to a distillation tower, where fractionation of various components in the crude oil mixture occurs with heating in a distillation column. The amount of heat energy supplied to the crude oil mixture in the distillation process depends in part upon the composition of the oil; in general, however, significant energy is expended in heating the crude oil during distillation, cooling the distillates, pressurizing the distillation column, and in other such steps. Within limits, certain refineries are capable of reconfiguration to handle differing crude oil feedstocks and products. In general, however, due to the relatively specialized refining apparatus, the ability of refineries to handle significantly different crude oil feedstocks is restricted.

In some embodiments, pretreatment of crude oil feedstocks using methods disclosed herein—including one or more cooling steps—can enhance the ability of a refining apparatus to accept crude oils having different compositions. For example, various chemical and/or physical properties of the crude oil mixture can be changed: lighter molecular weight components with lower viscosities can be produced from heavier components with higher viscosities; and certain components can be isomerized. The newly formed isomers can have lower viscosities than the components from which they are formed. The lighter molecular weight components and/or isomers with lower viscosities can then be introduced into the refinery, enabling processing of crude oil feedstock while may not have been suitable for processing initially.

In general, the various components of crude oil distill at different temperature ranges, corresponding to different vertical heights in a distillation column. Typically, for example, a refinery distillation column will include product streams at a large number of different temperature cut ranges, with the lowest boiling point (and, generally, smallest molecular weight) components drawn from the top of the column, and the highest boiling point, heaviest molecular weight components drawn from lower levels of the column. As an example, light distillates extracted from upper regions of the column typically include one or more of aviation gasoline, motor gasoline, napthas, kerosene, and refined oils. Intermediate distillates, removed from the middle region of the column, can include one or more of gas oil, heavy furnace oil, and diesel fuel oil. Heavy distillates, which are generally extracted from lower levels of the column, can include one or more of lubricating oil, grease, heavy oils, wax, and cracking stock. Residues remaining in the still can include a variety of high boiling components such as lubricating oil, fuel oil, petroleum jelly, road oils, asphalt, and petroleum coke. Certain other products can also be extracted from the column, including natural gas (which can be further refined and/or processed to produce components such as heating fuel, natural gasoline, liquefied petroleum gas, carbon black, and other petrochemicals), and various by-products (including, for example, fertilizers, ammonia, and sulfuric acid).

Generally, treatment of crude oil and/or components thereof using the methods disclosed herein can be used to modify molecular weights, chemical structures, viscosities, solubilities, densities, vapor pressures, and other physical properties of the treated materials. In general, a large number of different processing protocols can be implemented, according to the composition and physical properties of the feedstock.

Prior to and/or following distillation in a refinery, crude oil and/or components thereof can undergo a variety of other refinery processes to purify components and/or convert components into other products.

(i) Catalytic Cracking

Catalytic cracking is a widely used refinery process in which heavy oils are exposed to heat and pressure in the presence of a catalyst to promote cracking (e.g., conversion to lower molecular weight products). Originally, cracking was accomplished thermally, but catalytic cracking has largely replaced thermal cracking due to the higher yield of gasoline (with higher octane) and lower yield of heavy fuel oil and light gases. Most catalytic cracking processes can be classified as either moving-bed or fluidized bed processes, with fluidized bed processes being more prevalent. Process flow is generally as follows. A hot oil feedstock is contacted with the catalyst in either a feed riser line or the reactor. During the cracking reaction, the formation of coke on the surface of the catalyst progressively deactivates the catalyst. The catalyst and hydrocarbon vapors undergo mechanical separation, and oil remaining on the catalyst is removed by steam stripping. The catalyst then enters a regenerator, where it is reactivated by carefully burning off coke deposits in air. The hydrocarbon vapors are directed to a fractionation tower for separation into product streams at particular boiling ranges.

Older cracking units (e.g., 1965 and before) were typically designed with a discrete dense-phase fluidized catalyst bed in the reactor vessel, and operated so that most cracking occurred in the reactor bed. The extent of cracking was controlled by varying reactor bed depth (e.g., time) and temperature. The adoption of more reactive zeolite catalysts led to improved modern reactor designs in which the reactor is operated as a separator to separate the catalyst and the hydrocarbon vapors, and the cracking process is controlled by accelerating the regenerated catalyst to a particular velocity in a riser-reactor before introducing it into the riser and injecting the feedstock into the riser.

The methods disclosed herein can be used before, during, and/or after catalytic cracking to treat components of crude oil. In particular, the methods disclosed herein can be used to pre-treat feedstock prior to injection into the riser, to treat hydrocarbons (including hydrocarbon vapors) during cracking, and/or to treat the products of the catalytic cracking process.

Cracking catalysts typically include materials such as acid-treated natural aluminosilicates, amorphous synthetic silica-alumina combinations, and crystalline synthetic silica-alumina catalysts (e.g., zeolites). During the catalytic cracking process, components of crude oil can be exposed to ions from one or more ion beams to increase the efficiency of these catalysts. For example, the crude oil components can be exposed to one or more different types of metal ions that improve catalyst activity by participating in catalytic reactions. Alternatively, or in addition, the crude oil components can be exposed to ions that scavenge typical catalyst poisons such as nitrogen compounds, iron, nickel, vanadium, and copper, to ensure that catalyst efficiency remains high. Moreover, the ions can react with coke that forms on catalyst surfaces to remove the coke (e.g., by processes such as sputtering, and/or via chemical reactions), either during cracking or catalyst regeneration.

(ii) Alkylation

In petroleum terminology, alkylation refers to the reaction of low molecular weight olefins with an isoparaffin (e.g., isobutane) to form higher molecular weight isoparaffins. Alkylation can occur at high temperature and pressure without catalysts, but commercial implementations typically include low temperature alkylation in the presence of either a sulfuric acid or hydrofluoric acid catalyst. Sulfuric acid processes are generally more sensitive to temperature than hydrofluoric acid based processes, and care is used to minimize oxidation-reduction reactions that lead to the formation of tars and sulfur dioxide. In both processes, the volume of acid used is typically approximately equal to the liquid hydrocarbon charge, and the reaction vessel is pressurized to maintain the hydrocarbons and acid in a liquid state. Contact times are generally from about 10 to 40 minutes, with agitation to promote contact between the acid and hydrocarbon phases. If acid concentrations fall below about 88% by weight sulfuric acid or hydrofluoric acid, excessive polymerization can occur in the reaction products. The use of large volumes of strong acids makes alkylation processes expensive and potentially hazardous. The methods disclosed herein can be used before, during, and/or after alkylation to treat components of crude oil.

(iii) Catalytic Reforming and Isomerization

In catalytic reforming processes, hydrocarbon molecular structures are rearranged to form higher-octane aromatics for the production of gasoline; a relatively minor amount of cracking occurs. Catalytic reforming primarily increases the octane of motor gasoline.

Typical feedstocks to catalytic reformers are heavy straight-run naphthas and heavy hydrocracker naphthas, which include paraffins, olefins, naphthenes, and aromatics. Paraffins and naphthenes undergo two types of reactions during conversion to higher octane components: cyclization, and isomerization. Typically, paraffins are isomerized and converted, to some extent, to naphthenes. Naphthenes are subsequently converted to aromatics. Olefins are saturated to form paraffins, which then react as above. Aromatics remain essentially unchanged.

During reforming, the major reactions that lead to the formation of aromatics are dehydrogenation of naphthenes and dehydrocyclization of paraffins. The methods disclosed herein can be used before, during, and/or after catalytic reformation to treat components of crude oil. Catalysts used in catalytic reformation generally include platinum supported on an alumina base. Rhenium can be combined with platinum to form more stable catalysts that permit lower pressure operation of the reformation process. Without wishing to be bound by theory, it is believed that platinum serves as a catalytic site for hydrogenation and dehydrogenation reactions, and chlorinated alumina provides an acid site for isomerization, cyclization, and hydrocracking reactions. In general, catalyst activity is reduced by coke deposition and/or chloride loss from the alumina support. Restoration of catalyst activity can occur via high temperature oxidation of the deposited coke, followed by chlorination of the support.

(iv) Catalytic Hydrocracking

Catalytic hydrocracking, a counterpart process to ordinary catalytic cracking, is generally applied to crude oil components that are resistant to catalytic cracking. A catalytic cracker typically receives as feedstock more easily cracked paraffinic atmospheric and vacuum gas oils as charge stocks. Hydrocrackers, in contrast, typically receive aromatic cycle oils and coker distillates as feedstock. The higher pressures and hydrogen atmosphere of hydrocrackers make these components relatively easy to crack.

In general, although many different simultaneous chemical reactions occur in a catalytic hydrocracker, the overall chemical mechanism is that of catalytic cracking with hydrogenation. In general, the hydrogenation reaction is exothermic and provides heat to the (typically) endothermic cracking reactions; excess heat is absorbed by cold hydrogen gas injected into the hydrocracker. Hydrocracking reactions are typically carried out at temperatures between 550 and 750° F., and at pressures of between 8275 and 15,200 kPa. Circulation of large quantities of hydrogen with the feedstock helps to reduce catalyst fouling and regeneration. Feedstock is typically hydrotreated to remove sulfur, nitrogen compounds, and metals before entering the first hydrocracking stage; each of these materials can act as poisons to the hydrocracking catalyst.

Most hydrocracking catalysts include a crystalline mixture of silica-alumina with a small, relatively uniformly distributed amount of one or more rare earth metals (e.g., platinum, palladium, tungsten, and nickel) contained within the crystalline lattice. Without wishing to be bound by theory, it is believed that the silica-alumina portion of the catalyst provides cracking activity, and the rare earth metals promote hydrogenation. Reaction temperatures are generally raised as catalyst activity decreases during hydrocracking to maintain the reaction rate and product conversion rate. Regeneration of the catalyst is generally accomplished by burning off deposits which accumulate on the catalyst surface. The methods disclosed herein can be used before, during, and/or after catalytic hydrocracking to treat components of crude oil.

(v) Other Processes

A variety of other processes that occur during the course of crude oil refining can also be improved by, or supplanted by, the methods disclosed herein. For example, the methods disclosed herein can be used before, during, and/or after refinery processes such as coking, thermal treatments (including thermal cracking), hydroprocessing, and polymerization to improve the efficiency and overall yields, and reduce the waste generated from such processes.

For example, the methods and systems disclosed herein can be used to make a variety of different products, or intermediate products that can be further processed into other products. For example, any of the disclosed mechanical processing methods can be used to make resin fiber composites that include resins such as polyethylene, polypropylene, and/or lignin.

A number of embodiments have been described. Nevertheless, it will be understood that various modifications may be made without departing from the spirit and scope of the invention. Accordingly, other embodiments are within the scope of the claims.

What is claimed is:

1. A method comprising:
   converting a cooled particulate biomass material to sugars in a mobile processing unit, wherein converting comprises utilizing an enzyme to saccharify cellulose in the biomass material to form sugars,
   wherein the biomass material is a lignocellulosic material and lignin has been separated from and removed from the lignocellulosic material prior to saccharifying,
   wherein the biomass material is cooled prior to converting and prior to removal of lignin from the lignocellulosic material,
   wherein the cooling step comprises cooling the biomass material to less than 0° C.,
   wherein the method further comprises irradiating the biomass material with electron beams and/or ion beams before or after the cooling step, and
   wherein the cooling and converting steps are performed while the biomass material is in transit.

2. The method of claim 1 further comprising grinding or comminuting the biomass material.

3. The method of claim 2 wherein comminuting is performed in a freeze grinding or freeze milling device.

4. The method of claim 1 wherein the cooled biomass material has a bulk density of less than 0.8 g/cm$^3$.

5. The method of claim 1 wherein the method further comprises fermenting the sugars to produce an alcohol.

6. The method of claim 1 wherein the material is in transit by ship, barge, train, or truck.

7. The method of claim 1 wherein the mobile processing unit is transportable by ship, barge, train, or truck.

* * * * *